United States Patent [19]

Vanek et al.

[11] Patent Number: 5,007,425
[45] Date of Patent: Apr. 16, 1991

[54] PATIENT AND COIL SUPPORT STRUCTURE FOR MAGNETIC RESONANCE IMAGERS

[75] Inventors: Denis W. Vanek, Cuyahoga Hts.; G. Neil Holland, Chagrin Falls, both of Ohio

[73] Assignee: Picker International, Inc., Highland Hts., Ohio

[21] Appl. No.: 234,313

[22] Filed: Aug. 19, 1988

[51] Int. Cl.$^5$ .............................................. A61B 5/055
[52] U.S. Cl. .......................... 128/653 A; 128/653 SC; 269/328
[58] Field of Search ...................... 128/653, 70, 71, 72, 128/73, 74; 324/307, 309, 318; 269/322, 328

[56] References Cited

U.S. PATENT DOCUMENTS

| | | | |
|---|---|---|---|
| 1,892,304 | 12/1932 | Hawley | 128/71 |
| 1,914,202 | 6/1933 | Henze et al. | 128/71 |
| 2,768,622 | 10/1956 | Sanders | 128/71 |
| 2,829,640 | 4/1958 | Moorman | 378/208 |
| 2,840,429 | 6/1958 | McDonald | 378/209 |
| 3,020,909 | 2/1962 | Stevens | 128/70 |
| 3,124,126 | 3/1964 | Spinks | 128/71 |
| 3,766,384 | 10/1973 | Anderson | 378/209 |
| 3,778,049 | 12/1973 | Viamonte, Jr. | 378/209 |
| 4,181,297 | 1/1980 | Nichols | 269/328 |
| 4,256,112 | 3/1981 | Kopf et al. | 269/328 |
| 4,354,499 | 10/1982 | Damadian | 128/653 |
| 4,527,124 | 7/1985 | van Uijen | 324/307 |
| 4,543,959 | 10/1985 | Sepponen | 324/309 |
| 4,567,894 | 2/1986 | Bergman | 128/653 |
| 4,592,362 | 6/1986 | Stedtfeld et al. | 128/653 |
| 4,724,386 | 2/1988 | Haacke et al. | 128/653 |

FOREIGN PATENT DOCUMENTS 3628035 2/1988 Fed. Rep. of Germany ...... 324/318
1128121 2/1985 U.S.S.R. .............................. 128/653

OTHER PUBLICATIONS

Simon, Howard E., *A Whole Body Nuclear Magnetic Resonance (NMR) Imaging System*, SPIE, vol. 273, Application of Optical Instrumentation in Medicine IX (1981) pp. 41–49.
Picker Health Care Products–Buyer's Guide, vol. 4, Picker Brochure, 1985.

*Primary Examiner*—Lee S. Cohen
*Assistant Examiner*—John D. Zele
*Attorney, Agent, or Firm*—Fay, Sharpe, Beall, Fagan, Minnich & McKee

[57] ABSTRACT

A support stand (B) adjustably supports either (i) a localized coil assembly or (ii) a portion of a patient within an image region of a magnetic resonance imager (A). A vertical member (42) extends upward from a base (40). A follower (44) is selectively positionable along the vertical member. In one embodiment, a universal joint (48) adjustably mounts a bracket (50) to the follower (FIG. 2). In another embodiment, the follower includes an arm (70) which receives a mounting pin (72) of the supported device. The supported device may be a surface coil (22) or an orthopedic appliance such as a knee support (80) or limb support (90). Every part of the support stand and the supported orthopedic structure, including screws and fasteners are constructed of a material which is invisible in the magnetic resonance images generated by the imager and which is a dielectric to avoid patient shock from induced currents.

5 Claims, 5 Drawing Sheets

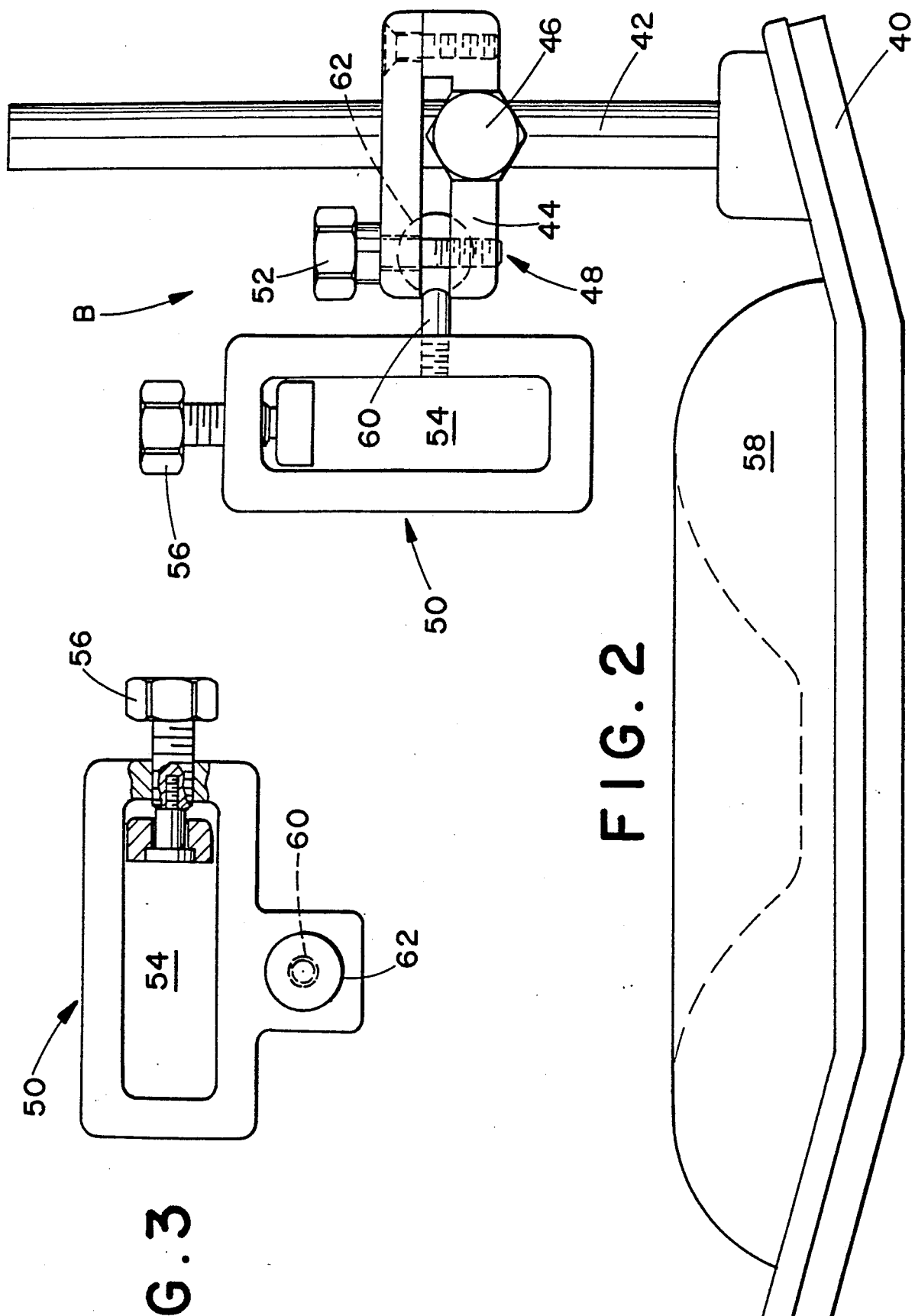

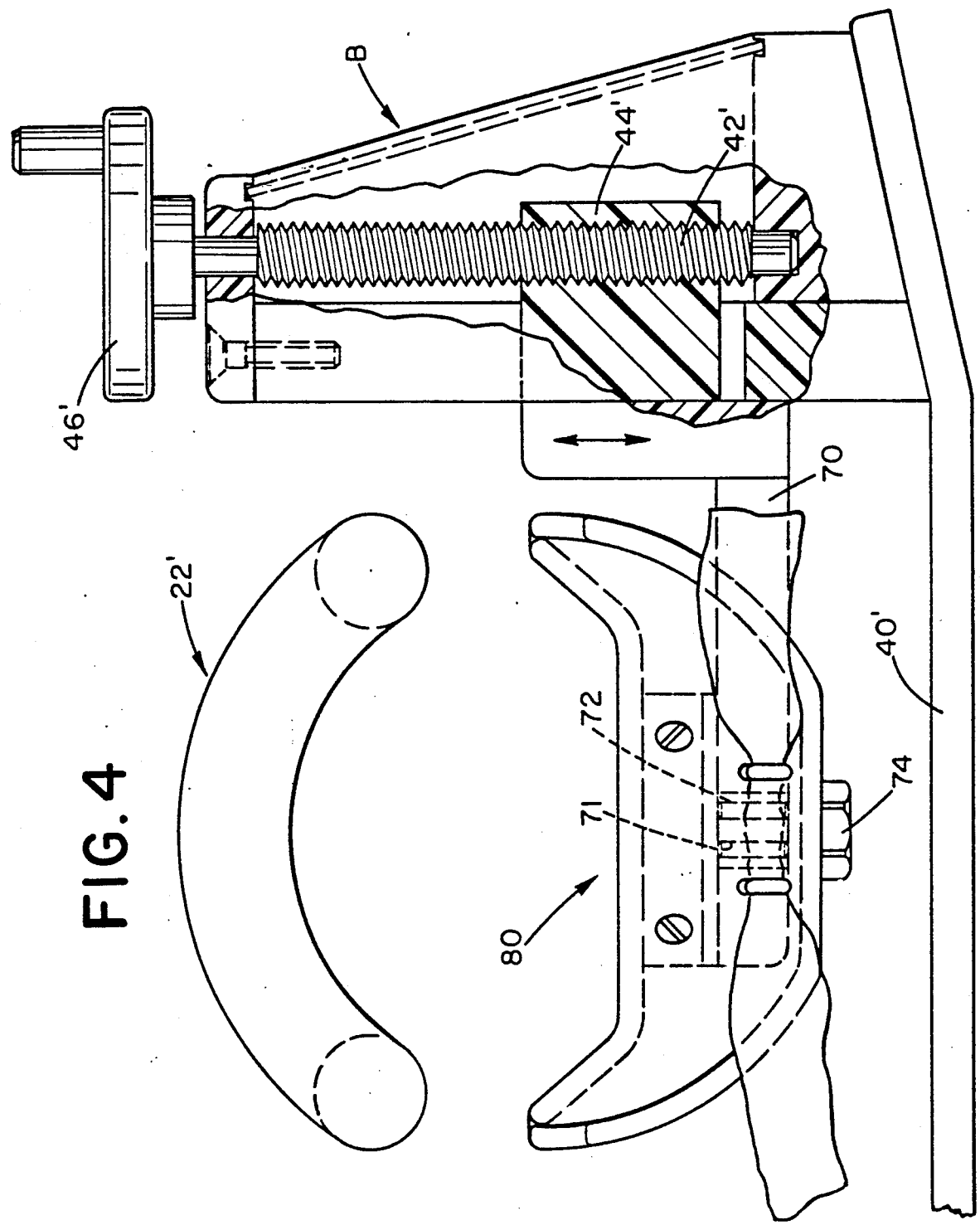

PATENT AND COIL SUPPORT STRUCTURE FOR MAGNETIC RESONANCE IMAGERS

BACKGROUND OF THE INVENTION

The present invention relates to support structures for diagnostic medical imaging devices. It finds particular application in conjunction with supporting patients and localized coils in magnetic resonance imagers. However, it is to be appreciated that the present invention may find limited application in conjunction with other diagnostic imaging apparatus or in supporting devices in magnetic resonance imagers.

Heretofore, localized or surface coils were utilized in conjunction with magnetic resonance imaging. The localized coils were pressed against a selected surface of the patient to be imaged, commonly with tape or straps. In other applications, a flat surface coil was disposed on the patient table and the patient laid on top of it.

For most magnetic resonance images, the patient laid flat on its back on the patient table. In those instances in which a supine position was inappropriate for the diagnostic imaging, foam cushions were inserted under or around appropriate portions of the patient. Typically, the cushions came inn various preselected shapes, such as wedges, donuts, and the like. For some applications, the coil was wedged between the patient and the cushion.

One of the drawbacks of fastening coils to the patient is image motion degradation attributable to patient movement. Further, the coils often caused patient discomfort during imaging depending on the location of the coil and the manner in which it was affixed to the patient. Positions in which the patient could be placed were limited by the size and shape of cushions at hand. Because foam cushions are relatively bulky, only a limited selection of cushions were normally kept readily available.

In accordance with the present invention, a positioning apparatus is provided which overcomes the above referenced problems.

SUMMARY OF THE INVENTION

In accordance with the present invention, a positioning apparatus is provided in combination with a magnetic resonance or other diagnostic imager. The positioning apparatus includes a support base, an upward standing portion, and an adjustable mounting means whose position is selectively adjustable. A surface coil, an orthopedic support, or other device is supported by the adjustable mounting means. The base, upward extending portion, and mounting means are all constructed of a material which is substantially invisible to magnetic resonance images so as not to obscure the portion of the patient being imaged.

In accordance with a more limited aspect of the present invention, the mounting means is vertically adjustable along the upward extending portion.

In accordance with another aspect of the present invention, a plurality of magnetically invisible orthopedic braces are provided, each orthopedic brace being selectively mountable in the mounting means.

In accordance with another more limited aspect of the invention, a plurality of surface coils are provided. Each surface coil is selectively mountable in the supporting means.

In accordance with another more limited aspect of the present invention, a joint means is provided such that the supported coil or orthopedic brace is selectively adjustable relative to three axes.

One advantage of the present invention is that it enables the relative position of a patient and surface coil to be readily adjusted.

Another advantage of the present invention is that it reduces motion artifacts.

Still further advantages of the present invention will become apparent to others upon reading and understanding the following detailed description of the preferred embodiments.

BRIEF DESCRIPTION OF THE DRAWINGS

The invention may take form in various parts and arrangements of parts or in various steps and arrangements of steps. The drawings are only for purposes of illustrating preferred embodiments and are not to be construed as limiting the invention.

FIG. 2 is an elevational view of a support stand for a localized coil;

FIG. 3 illustrates an alternate mounting bracket for the stand of FIG. 2;

FIG. 4 is an elevational view of an alternate embodiment of the support stand in combination with a knee support;

DETAILED DESCRIPTION OF THE PREFERRED EMBODIMENTS

Figure 1:
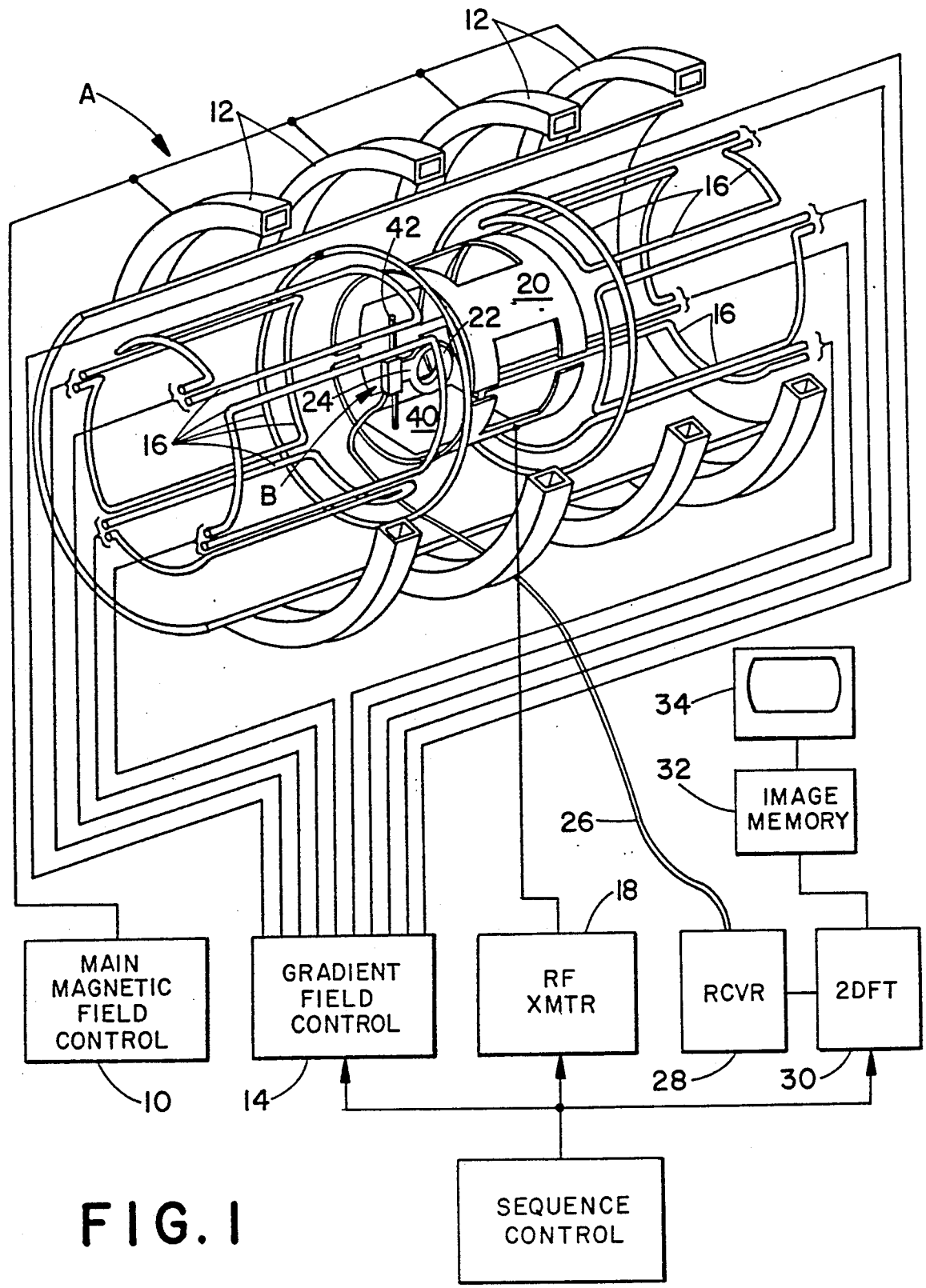
FIG. 1 is a magnetic resonance imaging apparatus in combination with a support stand and localized coil in accordance with the present invention.

With reference to FIG. 1, a magnetic resonance imaging apparatus A includes a main magnetic field generating means for establishing a generally uniform, static magnetic field longitudinally through a region of interest. The magnetic field means includes a magnetic field control circuit 10 and a plurality of resistance or superconducting magnets 12. A gradient field means selectively produces magnetic field gradients across and along the main magnetic field. A gradient magnetic field control circuit or means 14 applies current pulses to gradient coils 16 to create the gradients in the main magnetic field. A resonance excitation means includes a radio frequency transmitter 18 and a radio frequency coil 20 for broadcasting radio frequency (RF) signals that excite and manipulate magnetic resonance of selected dipoles within the image region.

A support stand B supports a localized or surface coil 22 which receives magnetic resonance signals emanating from the resonating dipoles of the subject. A preamplifier 24 mounted or supported by the stand and mounted closely adjacent the surface coil amplifies the magnetic resonance signals before transmission along a cable 26 that connects the surface coil 222 with a receiver 28. An image reconstruction means 30 such as an inverse two dimensional Fourier transform algorithm converts the magnetic resonance data from the receiver into an image representation. The image representation may be stored in an image memory means 32, displayed on a video monitor or other display means 34, subject to further processing, or the like.

With reference to FIG. 2, the stand B includes a base 40 which is configured to rest firmly on a patient supporting table or surface of the magnetic resonance imager A in the imaging region. An upstanding portion or rod 42 extends vertically from the base 40 to accommodate vertical positioning of a follower or 44. In the embodiment of FIG. 2, the follower 44 is slidably and rotatably mounted on the rod 42. A threaded member 46 selectively fixes the height and rotational position of the follower 44 relative to the rod 42. A joint means 48 which has three degrees of freedom, such as a ball and socket joint, mounts a bracket means 50 to the follower 44. The joint 47 enables the bracket 50 to be selectively positioned relative to three axes. A locking means 52 selectively locks the position of the joint 48 to fix the position of the bracket 50 and supported coil or orthopedic apparatus.

The bracket 50 defines an aperture 54 therein for receiving a mating projection of the supported device. A clamping means 56 selectively clamps the supported device in the bracket. Optionally, a pillow 58 may be disposed on the base 40, particularly when the supported apparatus is a localized coil configured for positioning adjacent the patient's head. All elements of the stand B illustrated in FIG. 2 are constructed of polyethylene or other strong plastic materials which do not adversely affect a resultant magnetic resonance image or conduct electrical currents.

In the embodiment of FIG. 2, the bracket 50 has a stem 60 projecting therefrom perpendicular to the aperture 54 on which a ball member 62 is fixedly mounted. The ball member is received in a mating socket of the joint means 48.

In the embodiment of FIG. 3, the bracket 50 has a mounting rod 60 which extends parallel rather than perpendicular to the axis of aperture 54. A ball member 62 is selectively receivable in the mating socket of the joint 48. The bracket embodied in FIG. 2 facilitates mounting the surface coil 22 in a vertical plane whereas the bracket embodiment of FIG. 3 facilitates mounting the coil in a horizontal plane. Of course, due to the three degrees of motion of the joint and the rotational adjustability of the follower 44, both brackets will enable the supported coil to be mounted at least to some extent in both vertical and horizontal planes.

Optionally, a plurality of followers 44 may be selectively mounted on the rod 42. One of the followers may support a bracket 50 which holds an orthopedic support and the other may hold a bracket that mounts a localized coil. Alternately, two localized coils or two orthopedic brackets could be mounted.

Figure 5:
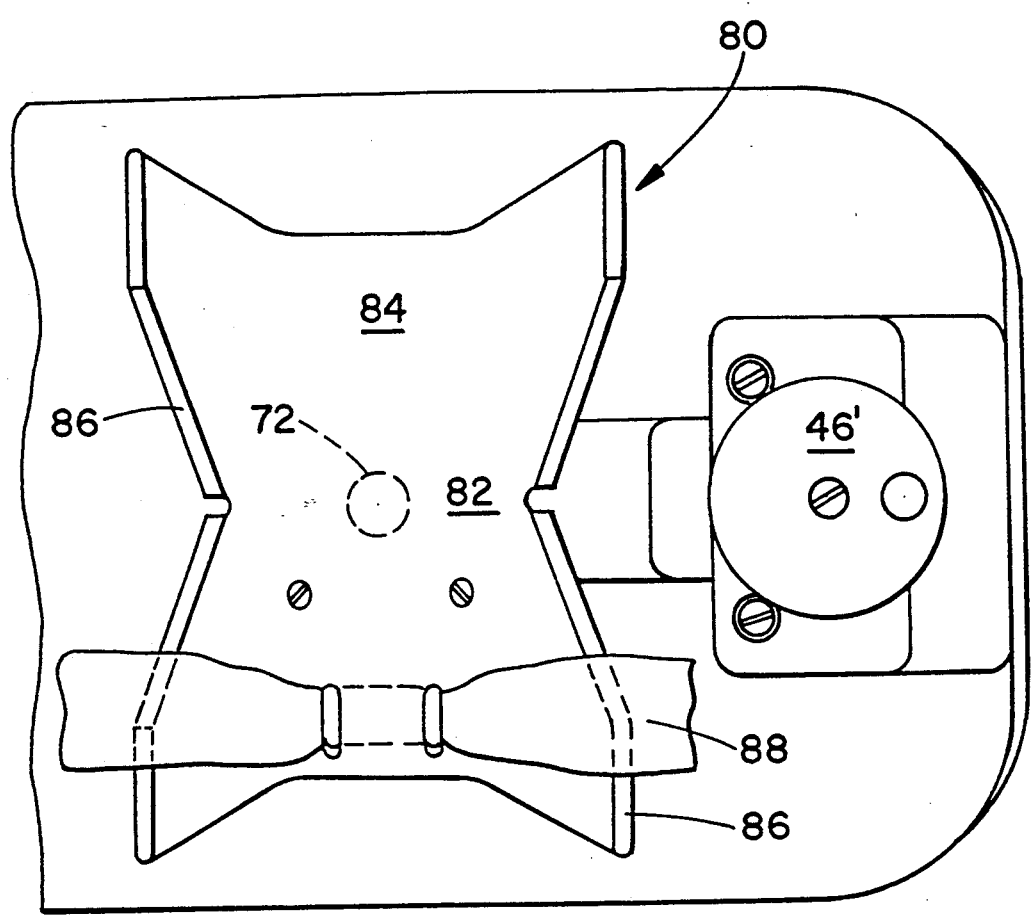
FIG. 5 is a top view of the stand and knee support of FIG. 4.

With reference to FIGS. 4 and 5, an alternate stand assembly B includes a base 40' and includes an upstanding vertical member or screw 42'. A follower 44' has a threaded interior bore such that it moves upward and downward relative to the base as a handle 46' is rotated. The pitch of threads is preferably such that the follower stays in a selected vertical position without locking the handle member 46'. An arm 70 depending from the follower has an aperture 71 at an outer end thereof for receiving a pin 72 which extends downward from the supported device. The downward extending pin 72 is preferably externally threaded such that a nut or other appropriate means 74 may be provided for locking the supported device to the support arm 70.

Figure 6:
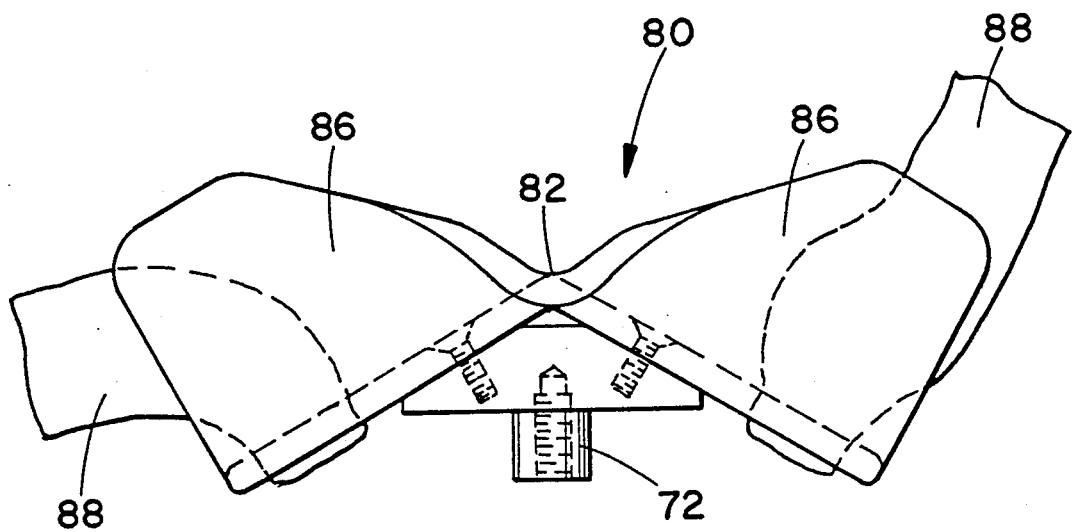
FIG. 6 is a side view of the knee support of FIG.

With continuing reference to FIGS. 4 and 5 and further reference to FIG. 6, the supported apparatus may be an angle rest orthopedic assembly or device 80 which is particularly adapted for supporting a patient's knee. The orthopedic support device includes an apex area 82 from which sloping portions 84 slope downward. The relative slope of portions 84 are selected such that they provide support to the calf and thigh when the apex area 82 is positioned under the knee. Optionally, an adjusting means may be provided for enabling the relative slope to be adjusted to accommodate different knee and leg positions. Upstanding side supports 86 provide side to side stability in the positioning of the patient's leg. VELCRO hook and loop fabric straps 88 may be fastened around the patient's leg to stabilize the positioning of the knee. Optionally, the VELCRO hook and loop fabric strips 88 may be wrapped around a surface coil 22' that is disposed on the knee. Specifically, the surface coil 22' has curved end portions which follow the top surface of the patient's thigh and calf and relatively straight side portions extending therebetween.

The support arm 70 may be adjustably mounted to the follower 44', particularly for rotation about a horizontal axis, such that the orientation of the support apparatus is selectively adjustable. The arm assembly may have a multisided surface which is receivable in a multi-sided aperture in any one of a plurality of fixed orientations, the plurality depending on the number of sides. Alternately, a continuously adjustable arrangement may be provided with a threaded member for clamping the two in a selected orientation.

Figure 7:
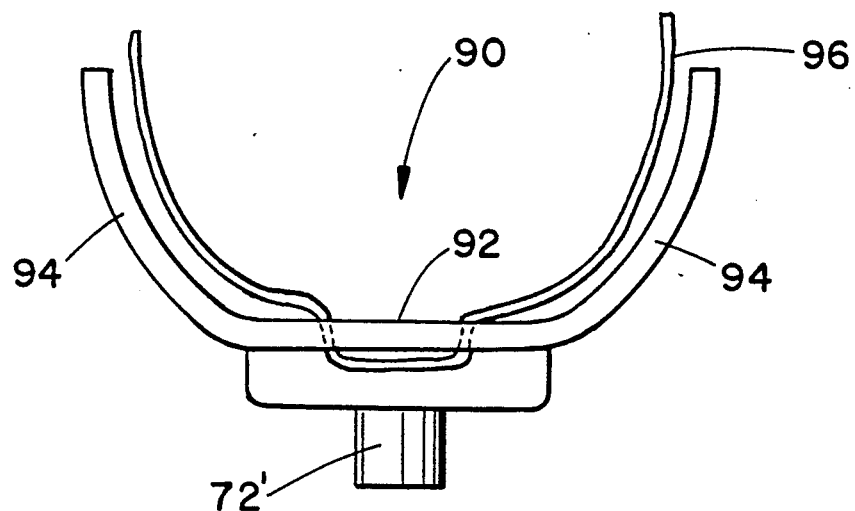
FIG. 7 illustrates a limb support which is selectively substitutable for the knee support brace of FIG. 4; and, FIG. 8 is a top view of the limb support of FIG. 7.
Figure 8:
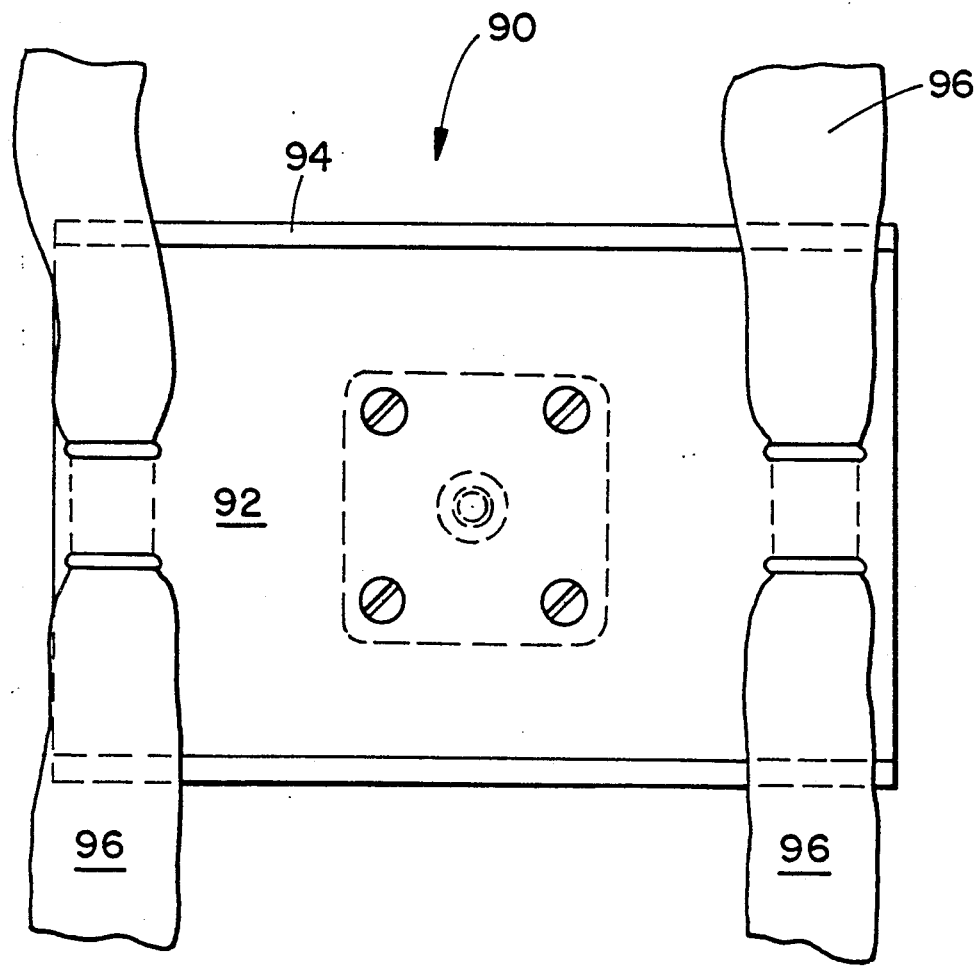

With reference to FIGS. 7 and 8, a straight limb support assembly 90 may be provided. The straight limb support assembly includes a relatively flat lower surface 92 with upper side constraints 94. A mounting pin 72' is selectively receivable in the aperture of arm 70 to be supported thereby. VELCRO hook and loop fabric strips 96' are provided for securely positioning the supported limb. The VELCRO hook and loop fabric strips enable the same straight limb support assembly to be used for forearm studies, calf studies, and the like.

The parts of the stand of FIGS. 4 and 5 and of the orthopedic supports of FIGS. 4–8 are again constructed of polyethylene or other plastics or materials that do not adversely affect the resultant magnetic resonance image. The materials are further not conductive such that the gradient magnetic fields and RF pulses are not apt to generate current flows therethrough. Accordingly, it is preferred that neither the stand nor the supported structure have any ferromagnetic or metallic parts.

The invention has been described with reference to the preferred embodiments. Obviously, modifications and alterations will occur to those of ordinary skill in the art upon reading and understanding the preceding specification. It is intended that the invention be construed as including all such alterations and modifications insofar as they come within the scope of the appended claims or the equivalents thereof.

Having thus described the preferred embodiment, the invention is now claimed to be:

1. A support stand which is selectively positionable within an image region of a magnetic resonance imaging apparatus that includes a means for establishing a static magnetic field through the image region, a means for causing magnetic field gradients across the static magnetic field, a means for inducing magnetic resonance of selected dipoles of a patient within the imaging region, a means for receiving magnetic resonance signals emanating from the resonating dipoles, and an image reconstruction means for reconstructing an image representation from the received magnetic resonance signals, the support stand comprising:
  a base constructed of a non-ferrous, non-conductive material;
  a non-ferrous, non-conductive screw rotatably and vertically mounted in the base;
  a follower which supports one of an orthopedic device and (ii) a resonance signal receiving coil, the follower being constructed of a non-ferrous, non-conductive material with a threaded vertical interior bore that threadedly receives the screw therein, the follower being movably supported on the screw too be raised and lowered by relative rotation therebetween.

2. A magnetic resonance imaging apparatus comprising:
  a means for establishing a static magnetic field through an imaging region;
  a means for causing magnetic field gradients across the static magnetic field;
  a means for inducing magnetic resonance of selected dipoles of a subject within the imaging region;
  a means for receiving magnetic resonance signals emanating from the resonating dipoles, the receiving means including a coil that is disposable contiguous to the resonating dipoles;
  a means for reconstructing an image representation from the received magnetic resonance signals; and,
  a support structure removable supported in the imaging region including:
    a base removably supported in the imaging region;
    an upstanding member extending upward therefrom;
    a follower which moves along and is vertically adjustable relative to the upstanding member, the upstanding member and follower having a threaded interengagement such that rotation of the upstanding member adjusts a vertical position of the follower therealong; and,
    a means connected with the follower for adjustably supporting relative to the subject at least one of (i) the coil and a (ii) limb of the subject.

3. The apparatus as set forth in claim 2 wherein the means connected with the follower includes an orthopedic device for supporting the subject's limb.

4. The apparatus as set forth in claim 3 wherein the orthopedic device has an apex portion with sloping portions to either side thereof for selectively supporting a knee of the subject.

5. The apparatus as set forth i claim 3 wherein the orthopedic device has a generally U-shaped cross-section for supporting the limb and hook and loop means for selectively securing the limb to the orthopedic device.

* * * * *